United States Patent
Hokkirigawa et al.

(10) Patent No.: US 6,777,042 B2
(45) Date of Patent: Aug. 17, 2004

(54) DEODORIZING AND ABSORBING MATERIAL

(75) Inventors: Kazuo Hokkirigawa, Yonezawa (JP); Motoharu Akiyama, Nagano-ken (JP); Noriyuki Yoshimura, Nagano-ken (JP)

(73) Assignee: Minebea Co., Ltd., Nagano-ken (JP)

( * ) Notice: Subject to any disclaimer, the term of this patent is extended or adjusted under 35 U.S.C. 154(b) by 21 days.

(21) Appl. No.: 10/154,790

(22) Filed: May 24, 2002

(65) Prior Publication Data

US 2002/0192469 A1 Dec. 19, 2002

(30) Foreign Application Priority Data

May 25, 2001 (JP) ........................................ 2001-157561

(51) Int. Cl.⁷ .............................................. B29D 22/00
(52) U.S. Cl. ................ 428/34.1; 428/307.3; 428/321.1; 428/402
(58) Field of Search ............................ 428/34.1, 307.3, 428/321.1, 402

(56) References Cited

FOREIGN PATENT DOCUMENTS

| JP | 200211203 | * 12/2002 |
| JP | 2001157551 | * 12/2002 |

OTHER PUBLICATIONS

Article: *Development of Hard and Porous Carbon Material "RB Ceramics" Using Rice Bran as a Starting Material*; (Translation from "Zairyou Kagaku", vol. 17, No. 6, pp. 24 to 27, May 1997); Kazuo Hokkirigawa; 10 pages.

* cited by examiner

Primary Examiner—Leszek B. Kiliman
(74) Attorney, Agent, or Firm—Flynn, Thiel, Boutell & Tanis, P.C.

(57) ABSTRACT

There is provided a deodorizing and absorbing material comprising RB ceramics and/or CRB ceramics as an odor absorbing material, which has excellent deodorizing properties and long term persistency thereof and is easily fabricated into a complicated shape when the material is used as a molded product.

9 Claims, 3 Drawing Sheets

CRB particle

Large pore
t>5μm
(Peak 15μm)

CRB resin

Middle pore
0.2μm<t<5μm
(Peak 1.8μm)

Carbonized rice bran

Hard glassy carbon
(Carbonized phenol resin)
Small pore
$t < 0.2 \mu m$
(Peak $0.05 \mu m$)

$Lc \approx 40 Å$
$La \approx 100 Å$

DEODORIZING AND ABSORBING MATERIAL

FIELD OF THE INVENTION

This invention relates to a novel deodorizing and absorbing material for deodorizing or absorbing an unpleasant odor or bad smell.

BACKGROUND OF THE INVENTION

Conventional deodorizing and absorbing materials are widely used to absorb and deodorize an odor in a car, room, refrigerator or freezer, or a bad smell from a toilet, clog cabinet, garbage box or kitchen garbage.

Properties of such deodorizing and absorbing materials have been variously improved, although it is desirable to further improve deodorizing properties or long-term persistency thereof, while there has been requested to develop a complexly shaped deodorizer which is used in a narrow space to absorb so-called air conditioner odor caused by bacterial or other contamination in air conditioners, especially those conditioners for cars.

SUMMARY OF THE INVENTION

Accordingly, it is an object of the present invention to provide a deodorizing and absorbing material of high absorbing properties and long-term durability which is easily molded into a complex shape.

PREFERRED EMBODIMENT OF THE INVENTION

Figure 1A:
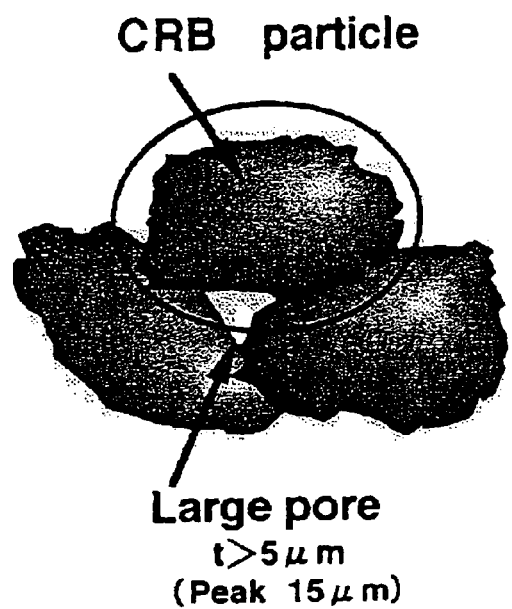
FIG. 1A is an illustration of relatively large pore of CRB ceramics.

The inventors have found that RB ceramics and CRB ceramics, as will be described later, physically absorb odorous ingredients because of porosity thereof and exhibit deodorizing and absorbing properties similarly as other porous material such as activated carbon.

The present invention has been completed on the basis of the above mentioned knowledge. That is, the present invention is to provide a deodorizing and absorbing material characterized in comprising RB ceramics and/or CRB ceramics.

RB ceramics is a porous carbon material obtained by the use of rice bran, which is by-produced 0.9 million ton/year or 33.3 million ton/year, and is known as investigation by Kazuo Hokkirigawa, the first inventor (see, Functional Material, Vol. 17, No. 5, pp. 24 to 28, May 1997).

RB ceramics is prepared by mixing and kneading a defatted product of rice bran and a thermosetting resin, press-molding the mixture to form a molded material, drying and then baking the dried material in an atmosphere of inert gas.

The defatted rice bran is not limited to a specific species and may either be Japanese or foreign one.

The thermosetting resin may be any resin which can be thermally set and typically includes phenol-, diarylphthalate-, unsaturated polyester-, epoxy-, polyimide- and triazine resins, although a phenol resin is preferably used.

A thermoplastic resin such as polyamide may be used together without departing from a scope of the present invention.

A mixing ratio of the defatted rice bran and the thermosetting resin is in the range of 50 to 90:50 to 10 and preferably 70 to 80:30 to 20 in weight ratio.

According to the above mentioned method, difference in ratio of shrinkage between the press-molded material and the baked material in an atmosphere of inert gas reached almost 25%, which made it substantially difficult to form a precision molded material but finally has been improved by developing CRB ceramics as a novel ceramic material.

The CRB ceramics used in the present invention is an improved material of RB ceramics obtained from defatted rice bran and a thermosetting resin and is prepared by mixing and kneading the defatted rice bran and the resin and primarily baking a mixture thus obtained in an inert gas at 700 to 1,000° C., followed by grinding to form carbonated powder, which is then mixed and kneaded with the thermosetting resin, press-molded and heat treated again in an atmosphere of inert gas at 100 to 1,100° C. to form a molded material.

The defatted rice bran used herein is not limited to a specific species and may either be Japanese or foreign one.

The thermosetting resin may be any resin which can be thermally set and typically includes phenol-, diarylphthalate-, unsaturated polyester-, epoxy-, polyimide- and triazine resins, although a phenol resin is preferably used. A thermosetting resin to be primarily baked is desirably liquid of relatively low molecular weight.

A mixing ratio of the defatted rice bran and the thermosetting resin is in the range of 50 to 90:50 to 10 and preferably 70 to 80:30 to 20 in weight ratio.

In general, primary baking is conducted by means of a rotary kiln for about 40 to 120 minutes.

A mixing ratio of the carbonated powder obtained through the primary baking and the thermosetting resin is in the range of 50 to 90:50 to 10 and preferably 70 to 80:30 to 20 in weight ratio.

A pressure for the press-molding the kneaded mixture of carbonated powder and thermosetting resin is in the range of 20 to 30 MPa and preferably 21 to 25 Mpa, while a mold die temperature is preferably about 150° C.

A well controlled electric furnace is generally used for the heat treatment and, on the other hand, a heat treating time is about 60 to 360 minutes.

A preferable heat treating temperature is 500 to 1,100° C., while a heat rising rate up to the heat treating temperature, especially up to 500° C., should be relatively slow, and in concrete terms, 0.5 to 2° C. per minute, and preferably about 1° C. per minute.

Further, it is necessary to lower the temperature relatively slowly down to 500° C. after the heat treatment is completed, followed by natural heat dissipation under 500° C. In concrete terms, such a slow down rate is 0.5 to 5° C. per minutes and preferably about 1° C. per minute.

An inert gas used for the primary baking and the heat treatment may include either one of helium, argon, neon and nitrogen gas, although nitrogen gas is preferable.

A thermoplastic resin such as polyamide may be used together with the above mentioned thermosetting resin without departing from a scope of the present invention.

CRB ceramics is a porous material having innumerable pores. These pores formed on CRB ceramics are classified into three kinds depending on a formation process thereof.

A pore shown in FIG. 1A is relatively large one having pore diameter of not less than 5 $\mu$m, which is formed as a space between CRB fine particles when they overlap each other. Peak pore value of this type is about 15 $\mu$m.

Figure 1B:
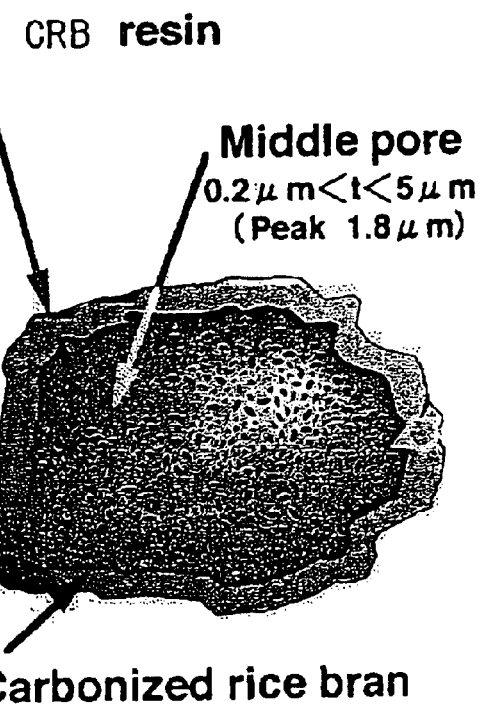
FIG. 1B is an illustration of pores of CRB ceramics caused by rice bran.

What is shown in FIG. 1B is a pore having pore diameter not more than 5 $\mu$m which is formed by fiber structure caused by rice bran. Peak pore value of this type is about 1.8 $\mu$m.

Figure 1C:
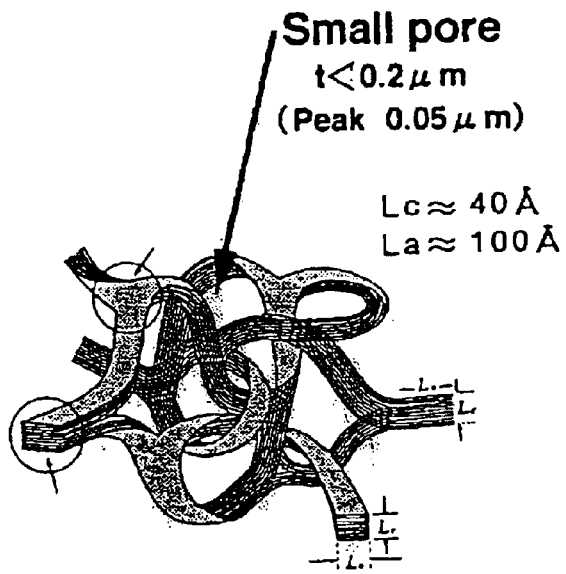
FIG. 1C is an illustration of pores of CRB ceramics caused by polymer chain.

A pore shown in FIG. 1C is small one having pore diameter of not more than 0.2 $\mu$m or less which is formed as a space between molecular chains of a high molecular polymer such as phenol resin when the polymer is carbonated at high temperature. Peak pore value of this type is about 0.05 $\mu$m.

It is thought that three kinds of pores formed in the CRB ceramics exhibit a specific absorbing effect corresponding to their pore diameter, respectively.

General properties of RB ceramics and CRB ceramics are as in the following:

extremely high hardness;

oil absorbing properties;

extremely small heat expansion coefficient;

porous structure;

electrical conductivity;

low specific gravity, light weighted;

improved abrasion resistance;

easiness of molding and mold die making;

capable of powdering; and less negative effects to global environment and more resource conservation due to rice bran to be used as a starting material.

As described above, these ceramic materials are porous, light in weight, hard and excellently abrasion resistant and thus useful as a deodorizing and absorbing material in the form of a molded material obtained therefrom or powder containing thereof.

The most typical distinction of RB and CRB ceramics is that difference in ratio of shrinkage between molded RB ceramics and a final product thereof is almost 25%, while that of CRB ceramics is so low as 3% or less, which makes the latter material much useful.

Thus, it is preferable to use the CRB ceramics of high dimensional accuracy when a deodorizing and absorbing material is provided as a molded product. However, the RB ceramics should not be excluded even in such a case. For example, the RB ceramics may be molded by means of a little bit larger mold die, which is then reduced to a desired size through secondary processing.

It is not necessary to consider the above mentioned difference in ratio of shrinkage and essentially either RB ceramics or CRB ceramics may be used when a deodorizing and absorbing material is provided as a powder.

One of characteristic features of the RB ceramics and/or CRB ceramics used in the present invention resides in porosity, which can be basically controlled by changing a baking condition and is generally increased with an increase in heat treating temperature. Porosity is greatly influenced by the baking temperature in the case of RB ceramics and by temperatures of primary and secondary heat treatments in the case of CRB ceramics. Temperatures of such baking or heat treatments at 800 to 1,000° C. yield a product of high porosity. A preferable range of porosity is selected as average pore diameter of 10 to 2,000 angstrom (1 to 200 nm) and pore volume of 0.1 to 1.1 cm$^3$/g.

When the present deodorizing and adsorbing material is a molded product, it may comprise RB ceramics and/or CRB ceramics as an ingredient thereof and, for example, may simply consist of RB ceramics and/or CRB ceramics, which has an advantage of easy molding workability.

Further, such a molded product may partially comprise RB ceramics and/or CRB ceramics, or may be a composite material of RB ceramics and/or CRB ceramics with other ceramics and a synthetic resin and/or elastomer, which have an advantage to increase mechanical strength or render it elastic.

Ceramics to be used together is one or two material selected from a group consisting of $SiO_2$, $Si_3N_4$, $ZrO_2$, $Al_2O_3$, SiC, BN, WC, TiC, sialon, porcelain clay, feldspathic clay and kaolin.

The above mentioned ceramics may be mixed with RB ceramics and/or CRB ceramics or used independently as a part of the molded product.

A molded product of this type may be used as a deodorizer for air conditioners, refrigerators, toilet stool, toilet seat, trash box, doorknobs, mouse of personal computers and other OA equipment, hand-strap rings, and the like.

When the present deodorizing and absorbing material comprises a powder of RB ceramics and/or CRB ceramics, various sorts or particle size of the power may be used depending on specific use and, in general, average particle size thereof is in the range of about 1 to 1,000 $\mu$m and preferably 1 to 500 $\mu$m.

The above mentioned powder is preferably kept in a breathable storage such as a bag or other package, case, box, container and the like made of porous material having a number of through holes, or breathable fabric, nonwoven fabric or traditional Japanese paper.

The powder of RB ceramics and/or CRB ceramics may be used together with an other powdery deodorizing and absorbing material such as activated carbon, zeolite, activated clay and clay minerals, or a known chemical deodorizing and absorbing material to complementarily increase a deodorizing effect. An example of the clay minerals includes a type of double-chain structure such as sepiolite, attapulgite and palygorskite. An example of the chemical deodorizing and absorbing material includes a metal salt such as sulfate, nitrate, chloride of a Zn, Al, Cu, Cr, Fe, Co, Ni, etc., the metal being divalent or higher valency.

A deodorizing and absorbing material comprising these salts of strong inorganic acids is neutralized by a reaction with an alkaline component such as ammonia, amine, etc., followed hydrolysis by moisture to form a weak base, which reacts with an acidic component such as hydrogen sulfide and mercaptan to cause deodorization. These metal salts are generally impregnated as a solution thereof to a deodorizing and absorbing material other than described above and dried to deposit thereon.

A ratio of a RB ceramics and/or CRB ceramics powder to the other powdery deodorizing and absorbing material is preferably 50 to 90:50 to 10 by weight.

Powdery particles of RB ceramics and CRB ceramics are hard and rough on the surface, which characteristically improves their maintainability as a powder.

The present invention will be summarized as in the following.

1. A deodorizing and absorbing material comprising RB ceramics and/or CRB ceramics as a material for absorbing odors.

2. A deodorizing and absorbing material described in the above item 1 in which the deodorizing and absorbing material is a molded product of RB ceramics or CRB ceramics.

3. A deodorizing and absorbing material described in the above item 2 in which a molded product comprises RB ceramics or CRB ceramics.

4. A deodorizing and absorbing material described in the above item 2 in which a molded product partially comprises RB ceramics or CRB ceramics.

5. A deodorizing and absorbing material described in the above item 2 or 4 in which a molded product is a composite material of RB ceramics or CRB ceramics and the other ceramics or a synthetic resin and/or elastomer.

6. A deodorizing and absorbing material described in the above item 1 in which RB ceramics and/or CRB ceramics is a powder.

7. A deodorizing and absorbing material described in the above item 6 in which an average particle diameter of powder is 1 to 1,000 $\mu$m.

8. A deodorizing and absorbing material described in the above item 6 or 7 which further comprises the other powdery deodorizing and absorbing material and/or a chemical deodorizing and absorbing material.

9. A deodorizing and absorbing material described in the above item 8 in which a powdery deodorizing and absorbing material is activated carbon, zeolite, activated clay and clay minerals.

10. A deodorizing and absorbing material described in the above item 8 in which a chemical deodorizing and absorbing material is one or more of sulfate, nitrate or chloride of a metal selected from Zn, Al, Cu, Cr, Fe, Co and Ni.

11. A deodorizing and absorbing material in which a deodorizing and absorbing material described in either one of the above items 6 to 10 is kept in a breathable container.

The present invention will be further described in the following examples. It should be understood that the present invention is not restricted by the examples.

EXAMPLE 1

A defatted product of rice bran in an amount of 75 kg and a liquid phenol resin (resol) in an amount of 25 kg were mixed and kneaded by heating at 50 to 60° C. to form a plastic and homogeneous mixture.

The mixture was molded into sphere of 3 cm in diameter and baked by means of a rotary kiln in a nitrogen atmosphere at 950° C. for 60 minutes. The carbonated material thus baked was ground by a grinder and further pulverized by means of a ball mill to yield a deodorizing and absorbing material comprising a RB ceramics powder having average particle size of 50 $\mu$m, average pore diameter of 0.05 $\mu$m and pore volume of 0.45 cm$^3$/g.

EXAMPLE 2

A deodorizing and absorbing material was prepared from a RB ceramics powder in a similar manner as described in Example 1 except that the baking temperature is 800° C. There was obtained a RB ceramics powder having average particle size of 150 $\mu$m, average pore diameter of 0.055 $\mu$m and pore volume of 0.43 cm$^3$/g.

EXAMPLE 3

A defatted product of rice bran in an amount of 75 kg and a liquid phenol resin (resol) in an amount of 25 kg were mixed and kneaded by heating at 50 to 60° C. to form a plastic and homogeneous mixture. The mixture was primarily baked by means of a rotary kiln in a nitrogen atmosphere at 950° C. for 60 minutes. The carbonated material thus baked was screened by means of a 300 mesh-screen to obtain a carbonated powder having particle size of 50 to 80 $\mu$m.

The carbonated powder thus obtained in an amount of 75 kg and a solid phenol resin (resol) in an amount of 25 kg were mixed and kneaded by heating at 100 to 150° C. to form a plastic and homogeneous mixture as a CRB ceramics precursor.

The CRB ceramics precursor was molded into sphere of 3 cm in diameter and baked in a nitrogen atmosphere at a secondary baking temperature of 800° C. for two hours. The carbonated material thus baked was ground by a grinder and further pulverized by means of a ball mill to yield a deodorizing and absorbing material comprising a CRB ceramics powder having average particle size of 20 $\mu$m, average pore diameter of 0.035 $\mu$m and pore volume of 0.55 cm$^3$/g.

EXAMPLE 4

A CRB ceramics powder was prepared in a similar manner as described in Example 3 except that a secondary baking temperature is 1,000° C. There was obtained a RB ceramics powder having average particle size of 100 $\mu$m, average pore diameter of 0.03 $\mu$m and pore volume of 0.7 cm$^3$/g.

EXAMPLE 5

A CRB ceramics precursor prepared in a similar manner as described in Example 3 was molded into an equilateral triangular prism shape of 5 cm in side×12 cm in height for the purpose of using in refrigerators, and baked by means of an electric furnace in a nitrogen atmosphere at a secondary baking temperature of 900° C. to form a deodorizing material for refrigerators having average pore diameter of 0.033 $\mu$m and pore volume of 0.64 cm$^3$/g.

EXAMPLE 6

Samples of deodorizing and absorbing materials prepared in Examples 1 to 5 in an amount of 50 cm$^3$ were put in a wide mouth container of 100 cm$^3$ in a opened situation without capping and kept in a refrigerator in an odorized atmosphere to examine a deodorizing effect thereof. Further, samples of deodorizing and absorbing materials prepared in Examples 1 to 5 in an amount of 50 cm$^3$ were put in a wide mouth container of 100 cm$^3$ in an opened situation without capping, kept in a refrigerator in an odorized atmosphere and, after allowing to stand for 20 days, subjected to a relative sensory evaluation test by ten panelists to examine changes in a deodorizing effect thereof in the refrigerator. The result obtained is shown in Table 1 below.

TABLE 1

|  | after 1 day | after 15 days | after 30 days |
|---|---|---|---|
| Example 1 | ○ | ○ | ○ |
| Example 2 | ○ | ○ | Δ |
| Example 3 | ○ | ○ | ○ |
| Example 4 | ○ | ○ | ○ |
| Example 5 | ○ | Δ | Δ |

In Table 1, each symbol ○, Δ and X designates excellent, good and not good effects, respectively.

EXAMPLE 6

Figure 2:
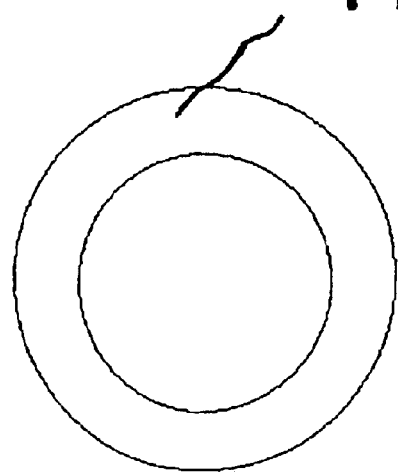
FIG. 2 is a schematic view of molded hand-strap ring comprising a deodorizing and absorbing material of the present invention.

A CRB ceramics precursor prepared in a similar manner as described in Example 3 was molded into a hand-strap ring of 15 cm in outer diameter and 13.5 cm in inner diameter as shown in FIG. 2. The thus molded product was baked in a nitrogen atmosphere at a secondary baking temperature of 700° C. for two hours. It was confirmed that the hand-strip ring comprising CRB ceramics 11 is mechanically strong and useful as a deodorizing and absorbing material.

EXAMPLE 7

Figure 3:
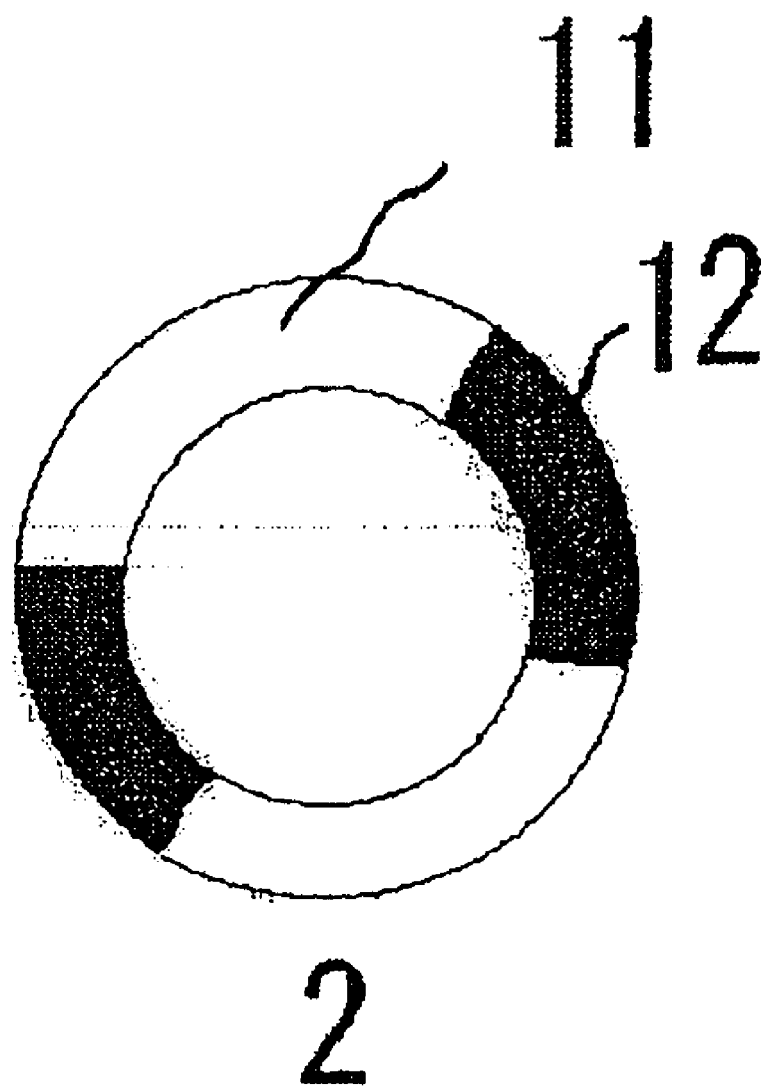
FIG. 3 is a schematic view of molded hand-strap ring partially comprising a deodorizing and absorbing material of the present invention.

A CRB ceramics precursor prepared in a similar manner as described in Example 3 was molded into a hand-strap ring of 15 cm in outer diameter and 13.5 cm in inner diameter as shown in FIG. 3 which comprises molded CRB ceramics 11 partially and molded alumina 12 as the other remaining part.

The thus molded product was baked in a nitrogen atmosphere at a secondary baking temperature of 900° C. for three hours. It was confirmed that the hand-strap ring comprising molded CRB ceramics 11 and molded alumina 12 is mechanically strong and useful as a deodorizing and absorbing material.

As has been described above, a deodorizing and absorbing material of the present invention has excellent deodorizing properties and long term persistency thereof, while it is possible to mold freely and fabricate easily into a complicated shape when the present material is provided as a molded product.

What is claimed is:

1. A deodorizing and absorbing material comprising RB ceramics and/or CRB ceramics as a material for absorbing odors.

2. A deodorizing and absorbing material according to claim 1, wherein a deodorizing and absorbing material is a molded product of RB ceramics or CRB ceramics.

3. A deodorizing and absorbing material according to claim 2, wherein a molded product comprises RB ceramics or CRB ceramics.

4. A deodorizing and absorbing material according to claim 2, wherein a molded product partially comprises RB ceramics or CRB ceramics.

5. A deodorizing and absorbing material according to claim 1, wherein RB ceramics and/or CRB ceramics is a powder.

6. A deodorizing and absorbing material according to claim 5, wherein an average particle diameter of powder is 1 to 1,000 $\mu$m.

7. A deodorizing and absorbing material according to claim 5, wherein a powdery deodorizing and absorbing material is activated carbon, zeolite, activated clay and clay minerals.

8. A deodorizing and absorbing material according to claim 5, wherein a chemical deodorizing and absorbing material is one or two of sulfate, nitrate or chloride of a metal selected from Zn, Al, Cu, Cr, Fe, Co and Ni.

9. A deodorizing and absorbing material in which a deodorizing and absorbing material according to claim 5 kept in a breathable storage.

* * * * *